United States Patent [19]

Pissiotas et al.

[11] Patent Number: 4,595,410

[45] Date of Patent: * Jun. 17, 1986

[54] OXIME DERIVATIVES OF DIPHENYL ETHERS AND THEIR USE IN HERBICIDAL COMPOSITIONS

[75] Inventors: Georg Pissiotas, Lörrach, Fed. Rep. of Germany; Otto Rohr, Therwil, Switzerland

[73] Assignee: Ciba-Geigy Corporation, Ardsley, N.Y.

[*] Notice: The portion of the term of this patent subsequent to Dec. 25, 2001 has been disclaimed.

[21] Appl. No.: 456,471

[22] Filed: Jan. 7, 1983

Related U.S. Application Data

[63] Continuation-in-part of Ser. No. 172,312, Jul. 25, 1980, Pat. No. 4,490,167.

[30] Foreign Application Priority Data

Aug. 6, 1979 [CH] Switzerland .................. 7197/79

[51] Int. Cl.⁴ ............... A01N 37/34; C07C 121/50; 558/406
[52] U.S. Cl. ............................... 71/105; 260/465 D
[58] Field of Search ................ 260/465 D; 71/105

[56] References Cited

U.S. PATENT DOCUMENTS 4,353,736 10/1982 Martin ............................ 71/105

FOREIGN PATENT DOCUMENTS 0034012 8/1981 European Pat. Off. .
2068949 8/1981 United Kingdom .

Primary Examiner—Delbert R. Phillips
Attorney, Agent, or Firm—Edward McC. Roberts; Frederick H. Rabin

[57] ABSTRACT

The invention relates to novel oxime derivatives of diphenyl ethers of the formula

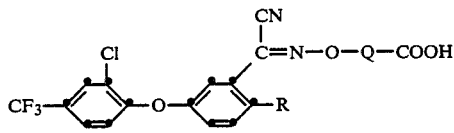

wherein R is hydrogen or halogen or a nitro or cyano group and Q is a straight-chain or branched $C_1$-$C_4$ alkylene bridge.

These compounds have good selective herbicidal action, they inhibit plant growth, and can be employed as safeners for protecting cultivated plants from the phytotoxic action of certain herbicides.

8 Claims, No Drawings

OXIME DERIVATIVES OF DIPHENYL ETHERS AND THEIR USE IN HERBICIDAL COMPOSITIONS

CROSS-REFERENCE TO RELATED APPLICATION

This is a continuation-in-part of our application Ser. No. 172,312, filed July 25, 1980, now U.S. Pat. No. 4,490,167.

The present invention relates to novel oxime derivatives of diphenyl ethers, processes for their production, herbicidal compositions containing them, and their use as herbicides and plant growth regulators or safeners, i.e. antidotes for herbicides which, when applied alone, would cause phytotoxic damage to certian crops of useful plants.

Diphenyloxyalkanoic acids having herbicidal properties are known from the prior art (e.g. German Offenlegungsschrift Nos. 2 136 828 and 2 433 067), as are also herbicidal phenoxybenzoic acids (e.g. German Offenlegungsschrift No. 2 784 635). Diphenyloximes have recently been disclosed in Belgian Pat. No. 870 068. The oxime derivatives of diphenyl ethers of this invention are able to control e.g. weeds of the species Galium, Veronica and Viola in cereal crops. Up to now, such control has only been possible to an insufficient degree with selective herbicides.

Accordingly, the present invention provides oxime derivatives of diphenyl ethers of the formula

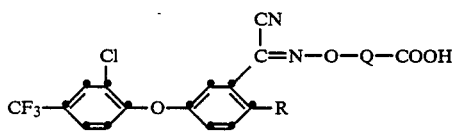

wherein R is hydrogen, halogen, or a nitro or cyano group, Q is a straight-chain or branched $C_1$-$C_4$alkylene bridge.

The compounds of the formula I are obtained by methods which are known per se.

In a first method, a halobenzene of the formula II

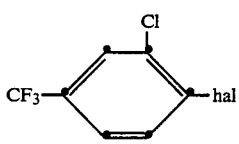

wherein $R_1$ and $R_2$ have the given meanings, is reacted with a m-hydroxybenzoate of the formula III

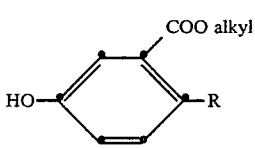

in the presence of a base, to give a diphenyl ether of the formula

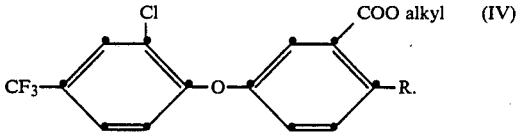

This diphenyl ether is treated, in an inert organic solvent, with lithium aluminium hydride or another reducing agent, until the ester group is reduced, to give a m-hydroxymethyl diphenyl ether of the formula V

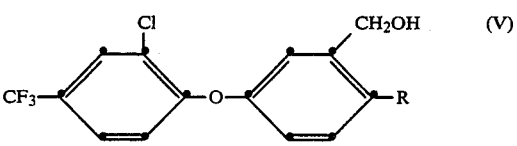

wherein R has the given meaning.

In this stage, the hydroxymethyl group is protected by esterification e.g. with a fatty acid, for example acetic acid, and then if R is hydrogen, another substituent R may be introduced by nitration, halogenation, or optionally by reducing the nitro group to an amino group and replacing this latter by another substituent by means of a Sandmeier reaction, or also by reaction of a halogen substituent with potassium cyanide, to give a diphenylmethoxy ester of the formula VI

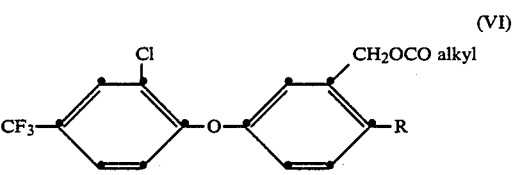

wherein R has the given meaning.

The fatty acid protective group is removed again by saponification with an inorganic base and the hydroxymethyl group is then converted with thionyl chloride or phosphoroxy chloride, or with thionyl bromide or phosphoroxy bromide, to the halomethyldiphenyl ether of the formula VII

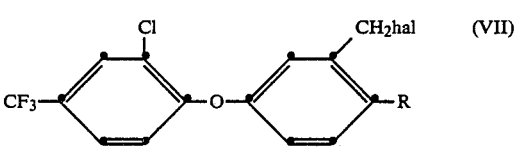

wherein hal is chlorine or bromine and R has the given meaning.

The halomethyldiphenyl ether of the formula VII is then converted with potassium cyanide or sodium cyanide to the corresponding cyanomethyl derivative (—$CH_2CN$). Reaction of this latter e.g. with pentyl nitrite ($C_5H_{11}ONO=O$), in the presence of sodium ethylate, yields an oxime salt of the formula VIII

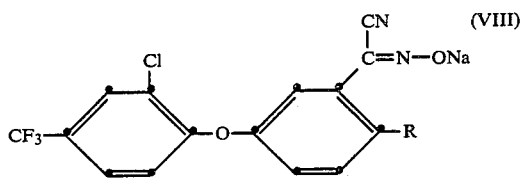

wherein R has the given meaning.

One process of this invention for producing the oxime ethers of the formula I comprises reacting the diphenyl ether oxime salt of the above formula VIII, in an inert organic solvent, with a compound of the formula IX $$Y-Q-COOH \qquad (IX)$$

wherein Y is a halogen atom or a removable acid radical and Q has the given meaning. Instead of the acid, an ester, preferably a lor alkyl- or benzyl ester of a compound of the formula IX can be used, which after addition to the diphenyl oxime is saponified.

A further method of synthesising compounds of the formula I consists in reacting the halobenzene of the formula II, in an inert organic solvent and in the presence of a base, with a m-hydroxybenzaldehyde or a m-hydroxyphenylketone of the formula X

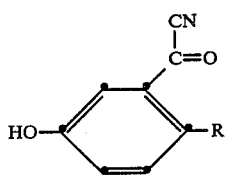

ps wherein R has the given meaning, to give a diphenyl aldehyde or ketone of the formula XI

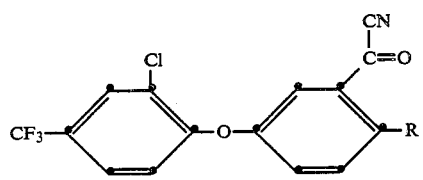

wherein R has the given meaning. This compound is converted with hydroxylamine (NH₂OH) to an oxime of the formula XII

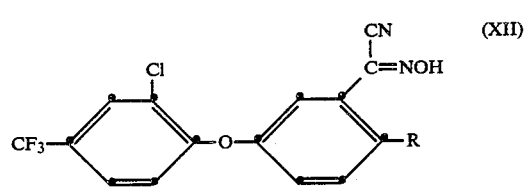

wherein R has the given meaning. This oxime is reacted with a compound of the formula IX, in an organic solvent and in the presence of a base, to give an oxime ether of the formula I. Instead of the acid, an ester, preferably a lower alkyl or benzyl ester of a compound of the formula IX can be used, which after addition to the diphenylether-oxime is saponified.

These reactions are carried out in the temperature range from 0° to 150° C. and in suitable solvents such as acetone, methyl ethyl ketone, acetonitrile, dimethyl formamide, or dimethyl sulfoxide.

Suitable bases are both inorganic bases such as alkali metal hydroxides and carbonates and bicarbonates of alkali metals and alkaline earth metals, and also dry ammonia, as well as organic bases, e.g. tertiary lower alkylamines such as triethylamine, trimethylamine or also cyclic amines, e.g. pyridine, collidine, or also aromatic amines such as dimethyl aniline.

These and other condensation reactions of α-oximino compounds and the alkali metal salts thereof with reactants Y-Q are described in "Organic Reactions", 1953, Vol. 7, pp. 343 and 373.

Oximes always exist in two stereoisomeric forms, the syn-form and anti-form. Throughout this specification, both stereoisomeric forms shall be understood as existing individually and as mixtures in any ratio.

The compounds (active ingredients) of the formula I are stable compounds which are soluble in conventional organic solvents, such as alcohols, ethers, ketones, dimethyl formamide, dimethyl sulfoxide etc.

The active ingredients of the formula I can be used by themselves, but more advantageously together with suitable carriers and/or other adjuvants, in the form of herbicidal compositions for controlling weeds.

In rates of application of 0.5 to 4 kg/hectare and more, the active ingredients and compositions which contain them have a pronounced herbicidal action especially on dicotyledonous weeds, such as Sida, Sesbania, Amaranthus, Sinapis, Ipomoea, Galium, Pastinak, Rumex, Matricaria, Chrysanthemum, Abutilon, Solanum etc. However, when employed in higher rates of application of at least 2 to 4 kg/hectare, a number of the active ingredients act on monocotyledonous weeds, such as Digitaria, Setaria and Echinochloa, whilst monocotyledonous cultivated plants, such as barley, wheat, maize, oats and rice, remain virtually undamaged at lower rates of application and suffer only minor damage at higher rates.

With these compounds, it has been possible to obtain good practical results in selectively controlling in particular dicotyledonous weeds in cereals, maize and rice. The most effective compounds have been found to be those having the structural formula

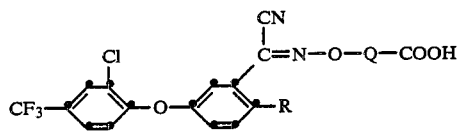

wherein R is chlorine or nitro and Q is as defined for formula I.

The active ingredients and compositions containing them can be employed as contact herbicides in pre-emergence application to sown cultivated areas, but preferably in postemercence application to weed-infested crops of cultivated plants.

The compositions of the present invention are obtained in known manner by intimately mixing and grinding active ingredients of the general formula I with suitable carriers and/or adjuvants, with or without the addition of anti-foam agents, wetting agents, dispersants and/or solvents which are inert to the active ingredients. The active ingredients can be processed to the following formulations:

solid formulations: dust, tracking powders, granules (coated granules, impregnated granules and homogeneous granules),
active ingredient concentrates which are of dispersible in water: wettable powders, pastes, emulsions, emulsifiable concentrates;
liquid formulations: solutions.

The following Examples describe in more detail the production of the compounds of the invention, the preparation of ready-for-use solid and liquid formulations or active ingredient concentrates, and biological tests to determine herbicidal action. Parts and percentages are by weight and pressures are indicated in millibars.

EXAMPLE 1

Production of 2-chloro-5-(2'-chloro-4'-trifluoromethylphenoxy)phenyl-acetonitrile oxime (carboyleth-1''-yl)ether (a) With stirring and under a nitrogen atmosphere, a solution of 45 g of methyl 3-(2-chloro-4-trifluoromethylphenoxy)benzoate (obtained by reaction of 3,4-dichlorobenzotrifluoride and methyl 3-hydroxybenzoate) in 60 ml of absolute ether is added dropwise at room temperature to a ready prepared mixture of 4 g of lithium aluminium hydride in 250 ml of absolute ether, such that the reaction mixture is kept moderately at the boil. When the addition is complete, stirring is continued for 1 hour under reflux. Remaining lithium aluminium hydride is destroyed by adding 5 ml of ethyl acetate and then a sufficient amount of 10% aqueous ammonium chloride solution is added dropwise until the formation of a readily filterable precipitate. After filtration, the ethereal phase is separated and the aqueous phase is extracted twice with ether. The combined ethereal phases are dried and then concentrated, affording 35.6 g of an oily product of the formula

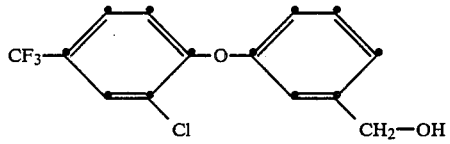

with a refractive index of $n_D^{25}$ 1.5424.

(b) Chlorine gas is introduced at a temperature of 20°–25° C. into a ready prepared mixture of 30.2 g of the compound obtained in (a) in 350 ml of glacial acetic acid until the starting material is consumed. The reaction mixture is then concentrated in vacuo and the oily residue is taken up in ether. The ethereal solution is washed twice with water, dried over sodium sulfate and concentrated, affording 38 g of a compound of the formua

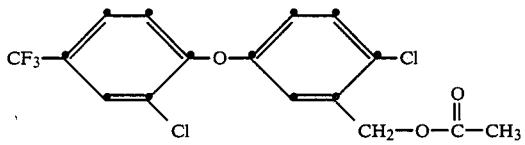

in the form of oil.

(c) 38 g of the acetate obtained in (b) is dissolved in 200 ml of methanol and the solution is reacted at room temperature for half an hour with 36 ml of 3.5N sodium hydroxide. After extraction with ether, the ethereal phase is washed three times with water, dried and concentrated, affording 32.5 g of the compound of the formula

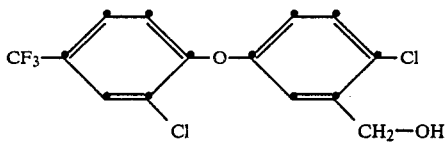

in the form of an oil with a refractive index of $n_D^{31}$ 1.5536.

(d) 4.5 ml of thionyl chloride are added dropwise at room temperature to a solution of 20 g of the alcohol obtained in (c) in 50 ml of toluene. After the evolution of gas has ceased, the reaction mixture is slowly heated and kept for 6 hours under reflux, then concentrated in vacuo, affording 20 g of the compound of the formula

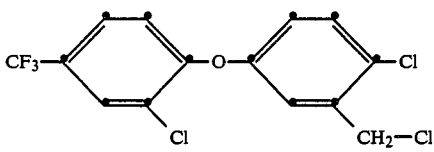

in the form of an oil.

(e) 20 g of the compound obtained in (d) are dissolved in 100 ml of dimethyl sulfoxide. With stirring, 9.4 g of sodium cyanide are added in portions, while keeping the temperature at 20°–25° C. The reaction mixture is then stirred for two hours and finally poured into ice-water and extracted with ether. The ethereal phase is washed three times with water, dried over sodium sulfate and concentrated, affording a product of the formula

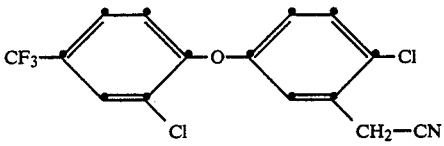

in a yield of 13.9 g and with a boiling point of 143° C./00.01 mbar.

(f) 11.4 g of the nitrile obtained in (e) are dissolved in a solution of 50 ml of ethanol and 2.3 g of sodium methylate, and then 4.4 ml of isopentyl nitrite are added dropwise at room temperature. The reaction mixture is stirred overnight and the product is precipitated with 100 ml of hexane. The precipitate is collected by filtration, affording 9.3 g of a product of the formula

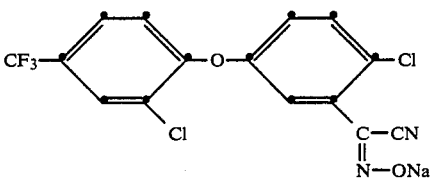

(g) 9.3 g of the sodium salt of the oxime obtained in (f) are dissolved in 50 ml of dimethyl formamide, and then 4 g of methyl 2-bromopropionate are added dropwise at room temperature. After stirring for 12 hours, the reaction mixture is poured into water and extracted with ether. The ethereal solution is dried over sodium sulfate and concentrated, affording 8.5 g of the compound of the formula

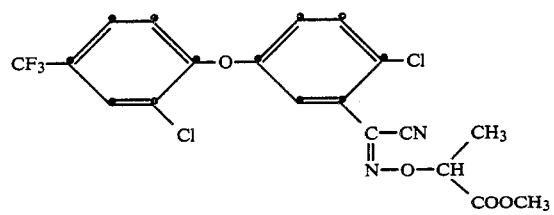

in the form of an oil with a refractive index of $n_D^{24}$ 1.5392.

(h) 5 g of the ester obtained in (g) are taken up in 20 ml of dioxan and 10 ml of 2n aqueous sodium hydroxide solution is added. The reaction mixture is then boiled under reflux for ½ hour, after which the solvent is distilled off, the reaction mixture cooled and rendered acid with concentrated hydrochloric acid. The reaction mixture is then extracted 3 times with ether, the etheral phase is collected, dried over sodium sulfate, treated with charcoal and evaporated. The residue is resinous colourless and consists of 4.5 g of 2-chloro-5-(2'-chloro-4'-trifluoromethylphenoxy)phenylacetonitrile oxime (carboxyl-eth-1"-yl)ether (compound No. 72).

According to this example, starting from 2-chloro-5-(2'-chloro-4'-trifluoromethylphenoxy)phenyl-acetonitrile oxime (ethoxycarbonyl-prop-1"-yl)ether $n_D^{25}$: 1.5303, resinous 2-chloro-5-(2'-chloro-4'-trifluoromethylphenoxy)phenylacetonitrile oxime (carboxyl-prop-1"-yl)ether (compound No. 73) was obtained and, starting from 2-chloro-5-(2'-chloro-4'-trifluoromethylphenoxy)phenyl-acetonitrile oxime (methoxycarbonyl-methyl)ether $n_D^{24}$: 1.5425, resinous 2-chloro-5-(2'-chloro-4'-trifluoromethylphenoxy)phenyl-acetonitrile oxime (carboxylmethyl)ether (compound No. 74) was obtained.

EXAMPLE 2

Preparation of ready-for-use solid and liquid formulations and active ingredient concentrates Granules The following substances are used to formulate 5% granules:
5 parts of an active ingredient of the formula I,
0.25 part of epoxidised vegetable oil,
0.25 part of cetyl polyglycol ether
3.50 parts of polyethylene glycol,
91 parts of kaolin (particle size 0.3–0.8 mm).

The active ingredient is mixed with epoxidised vegetable oil and the mixture is dissolved in 6 parts of acetone; the polyethylene glycol and cetyl polyglycol ether are then added. The resultant solution is sprayed on kaolin, and the acetone is subsequently evaporated in vacuo.

Wettable Powder

The following constituents are used to formulate (a) a 70% and (b) a 10% wettable powder:

(a)

70 parts of an active ingredient of the formula I,
5 parts of sodium dibutylnaphthylsulfate,
3 parts of naphthalenesulfonic acid/phenolsulfonic acid/formaldehyde condensate (3:2:1),
10 parts of kaolin,
12 parts of Champagne chalk;

(b)

10 parts of an active ingredient of the formula I,
3 parts of a mixture of the sodium salts of saturated fatty alcohol sulfates,
5 parts of naphthalenesulfonic acid/formaldehyde condensate,
83 parts of kaolin.

The respective active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to ingredient. These suspensions are suitable for controlling weeds in cultivations of plants.

Paste

The following substances are used to formulate a 45% paste:
45 parts of an active ingredient of the formula I,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active ingredient is intimately mixed with the additives in appropriate devices and ground. By diluting the resultant paste with water, it is possible to prepare suspensions of the desired concentration.

Emulsifiable Concentrate

The following ingredients are mixed to formulate a 25% emulsifiable concentrate:
25 parts of an active ingredient of the formula I,
5 parts of a mixture of nonylphenolpolyoxyethylene and calcium dodecylbenzenesulfonate,
15 parts of cyclohexanone,
55 parts of xylene.

This concentrate can be diluted with water to give emulsions in suitable concentrations of e.g. 0.1 to 10%.

EXAMPLE 3

Test methods for determining the herbicidal action
Pre-emergence herbicidal action (germination inhibition)

In a greenhouse, seeds of test plants are sown in flower pots having a diameter of about 15 cm, such that 12–25 plants can develop in each pot. Directly after sowing, the flower pots are treated with an aqueous suspension of active ingredient obtained by diluting an active ingredient concentrate with water. The concentration of active ingredient is calculated such that it can be expressed in kg per hectare. The pots are then kept in the greenhouse under the same constant conditions (22°–25° C., 50–70% relative humidity, and regular watering). The test is evaluated after 21 days and the condition of the plants is noted according to the following scale of ratings:
1: plant destroyed or has not germinated
2.3: severe damage, plant cannot recover
4.5: medium damage, plant stunted
6–9: slight damage, plant can recover 9: plant grows like untreated control.

The results are as follows:

|  | No. | | |
|---|---|---|---|
| compound tested | 72 | 73 | 74 |
| application rate in kg/ha | 421 | 421 | 421 |
| plant: | | | |
| wheat | 999 | 999 | 999 |
| abutilon | 235 | 445 | 123 |
| chenopodium album | 111 | 111 | 111 |
| sinapis alba | 124 | 444 | 112 |
| galium aparine | 444 | 456 | 123 |
| viola tricolor | 111 | 111 | 112 |

Post-emergence herbicidal action (contact herbicide)

Seeds of both monocotyledonous and dicotyledonous plants and weeds are sown in a greenhouse in flower pots of about 13 cm diameter, such that 12–25 plants are able to develop in each pot. The plants are allowed to germinate and, when they have reached the 4–6 leaf stage after about 2 weeks, they are treated with an aqueous active ingredient suspension. The suspension is obtained by diluting an active ingredient concentrate with water. The amount of active ingredient is such that the concentration can be expressed in kg per hectare. After the treatment, the pots are kept in the greenhouse under the same conditions as in the pre-emergence test. The test is evaluated 15 days after treatment and the results are given below:

|  | No. | | |
|---|---|---|---|
| compound tested | 72 | 73 | 74 |
| application rate in kg/ha | 21½ | 21½ | 21½ |
| plant: | | | |
| wheat | 577 | 689 | 679 |
| rice | 899 | 799 | 789 |
| abutilon | 113 | 124 | 113 |
| chenopodium album | 123 | 123 | 112 |
| xanthium sp. | 133 | 224 | 114 |
| ipomoea purpurea | 122 | 224 | 122 |
| sinapis alba | 111 | 111 | 111 |
| galium aparine | 122 | 234 | 223 |
| viola tricolor | 111 | 111 | 111 |

We claim:

1. An oxime derivative of a diphenyl ether of the formula I

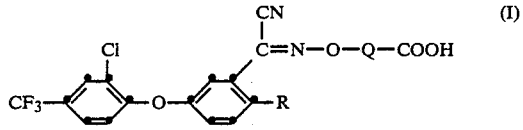

wherein R is hydrogen, halogen, or a nitro or cyano group, and Q is a straight-chain or branched $C_1$–$C_4$ alkylene bridge.

2. An oxime derivative of the formula I according to claim 1, wherein R is a chlorine atom or the nitro group.

3. 2-Chloro-5-(2'-chloro-4'-trifluoromethylphenoxy)-phenyl-acetonitrile oxime (carboxyl-eth-1''-yl)ether according to claim 2 of the formula

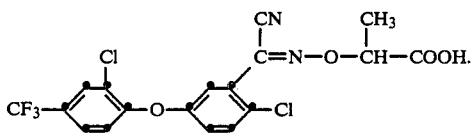

4. 2-Chloro-5-(2'-chloro-4'-trifluoromethylphenoxy)-phenyl-acetonitrile oxime (carboxyl-prop-1''-yl)ether according to claim 2 of the formula

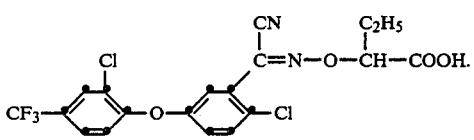

5. 2-Chloro-5-(2'-chloro-4'-trifluoromethylphenoxy)-phenyl-acetonitrile oxime (carboxylmethyl)ether according to claim 2 of the formula

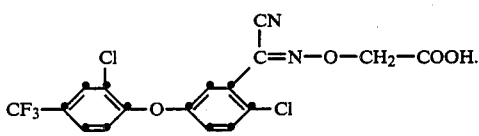

6. A herbicidal composition which comprises a herbicidally active amount of at least one oxime derivative of a diphenyl ether according to claim 1, and a carrier.

7. A method of selectively controlling weeds in crops of cultivated plants, which comprises applying to said crops a herbicidally effective amount of a compound according to claim 1.

8. A method of selectively controlling weeds in cereals crops, which comprises applying to said crops a herbicidally effective amount of a compound according to claim 1.

* * * * *